(12) United States Patent
Hoernig et al.

(10) Patent No.: US 9,836,860 B2
(45) Date of Patent: Dec. 5, 2017

(54) MULTIMODE X-RAY APPARATUS AND METHOD FOR THE OPERATION

(71) Applicant: Siemens Aktiengesellschaft, Munich (DE)

(72) Inventors: Mathias Hoernig, Erlangen (DE); Thomas Mertelmeier, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 141 days.

(21) Appl. No.: 14/796,274

(22) Filed: Jul. 10, 2015

(65) Prior Publication Data
US 2016/0012616 A1 Jan. 14, 2016

(30) Foreign Application Priority Data
Jul. 10, 2014 (DE) .................. 10 2014 213 412

(51) Int. Cl.
*A61B 6/00* (2006.01)
*G06T 11/00* (2006.01)
*G06T 5/00* (2006.01)

(52) U.S. Cl.
CPC ............ *G06T 11/005* (2013.01); *A61B 6/466* (2013.01); *A61B 6/502* (2013.01); *A61B 6/5205* (2013.01);
(Continued)

(58) Field of Classification Search
CPC ....... A61B 6/466; A61B 6/502; A61B 6/5205; A61B 6/5282; A61B 6/54; A61B 6/563; A61B 6/032; A61B 6/12; A61B 6/5235; A61B 6/4441; A61B 6/481; A61B 6/504; A61B 6/487; A61B 6/5247; A61B 6/025; A61B 34/20; A61B 6/4085; A61B 6/5217; A61B 5/055; A61B 6/03; A61B 6/503; A61B 6/02; A61B 6/4035; A61B 6/405; A61B 6/4233; A61B 6/4291; A61B 6/482; A61B 6/50; A61B 6/4417; A61B 8/0825; A61B 8/483; A61B 34/30; A61B 6/037; A61B 6/461; A61B 6/467; A61B 6/488; A61B 6/5211; A61B 6/544; A61B 6/545;
(Continued)

(56) References Cited

U.S. PATENT DOCUMENTS 7,831,296 B2 * 11/2010 DeFreitas .............. A61B 6/502
378/37
8,238,649 B2 * 8/2012 Stanton ................ G01N 23/046
378/4
(Continued)

FOREIGN PATENT DOCUMENTS

DE   10 2012 200 150 A1   7/2013

*Primary Examiner* — Irakli Kiknadze
(74) *Attorney, Agent, or Firm* — Schiff Hardin LLP

(57) ABSTRACT

In a method for producing 2-D recordings and 3-D recordings of a breast of a patient using an x-ray device that is operable in two recording modes and that has an x-ray radiation source and an x-ray radiation detector, the breast is placed between the x-ray radiation source and the x-ray radiation detector, and the 2-D recordings and the 3-D recordings are generated with the same breast placement. In order to keep the radiation exposure as low as possible in such a multi-mode x-ray device, all recordings are produced without the use of an anti-scatter grid, and a retroactive scattered radiation correction is implemented.

4 Claims, 3 Drawing Sheets

(52) U.S. Cl.
CPC .............. *A61B 6/5282* (2013.01); *A61B 6/54* (2013.01); *G06T 5/002* (2013.01); *A61B 6/563* (2013.01); *G06T 2207/10081* (2013.01); *G06T 2207/10116* (2013.01); *G06T 2207/30068* (2013.01); *G06T 2210/41* (2013.01); *G06T 2211/421* (2013.01)

(58) Field of Classification Search
CPC .................... A61B 8/14; G06T 11/005; G06T 2207/10081; G06T 2207/10116; G06T 2207/30068; G06T 2210/41; G06T 2211/421; G06T 5/002; G06T 11/008; G06T 11/003; G06T 11/006; G06T 2211/408; G01N 23/046; G01N 2223/419; G01N 2223/423; G01N 23/04
USPC ...................................... 378/6, 7, 37, 62, 70
See application file for complete search history.

(56) References Cited

U.S. PATENT DOCUMENTS

| | | | |
|---|---|---|---|
| 2003/0095624 A1 | 5/2003 | Eberhard et al. | |
| 2007/0268998 A1 | 11/2007 | Tu | |
| 2008/0013673 A1 | 1/2008 | Ruhmschopf | |
| 2012/0063566 A1* | 3/2012 | Smith | A61B 6/025 378/37 |
| 2015/0182191 A1* | 7/2015 | Caluser | A61B 5/4312 600/440 |

* cited by examiner

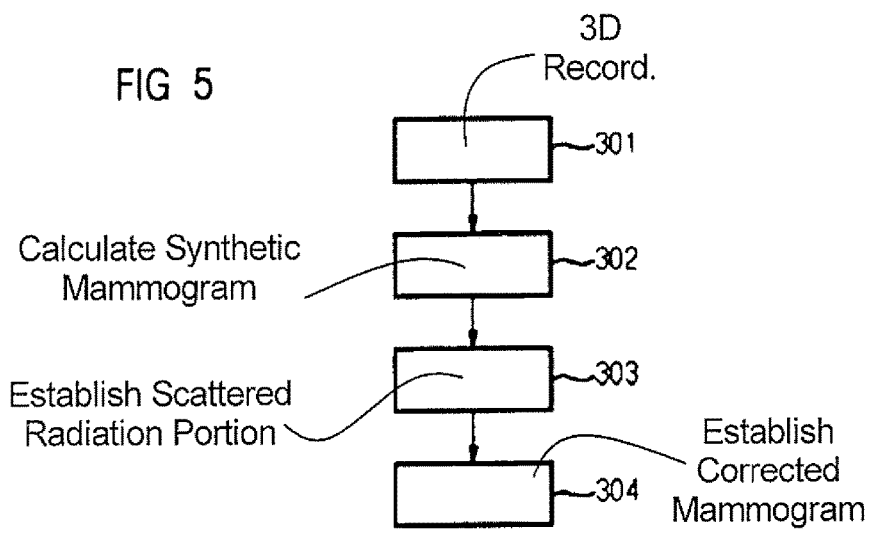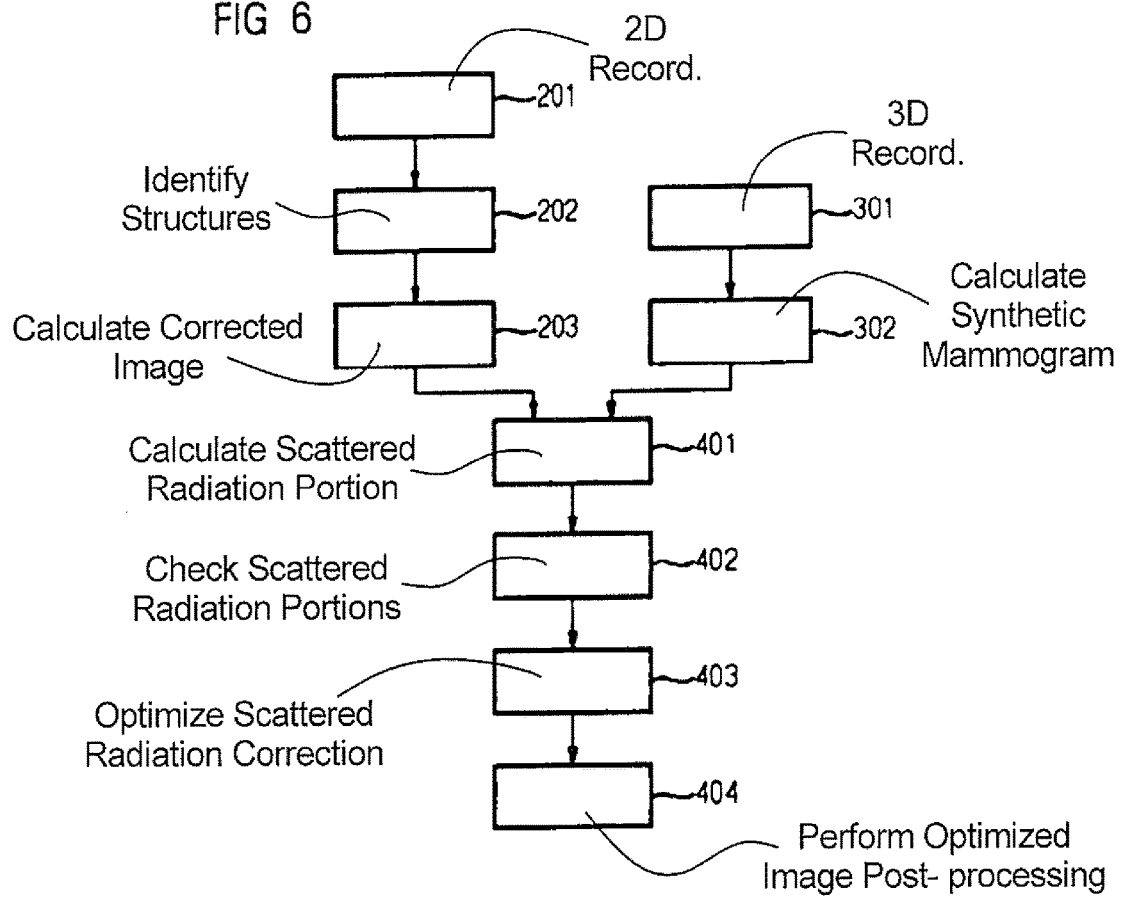

MULTIMODE X-RAY APPARATUS AND METHOD FOR THE OPERATION

BACKGROUND OF THE INVENTION

Field of the Invention

The invention concerns a method for producing 2-D recordings and 3-D recordings of a breast of a patient using an x-ray apparatus of the type that is operable in two recording modes and that has an x-ray radiation source and an x-ray radiation detector, wherein the breast is placed between the x-ray radiation source and the x-ray radiation detector, wherein the 2-D recordings and the 3-D recordings are generated with the same breast placement.

Moreover, the invention concerns an x-ray apparatus that is operable in two recording modes, designed for producing 2-D recordings and 3-D recordings of a breast of a patient, of the type having an x-ray radiation source and an x-ray radiation detector, wherein the breast is placeable between the x-ray radiation source and the x-ray radiation detector, wherein the 2-D recordings and 3-D recordings are producible with the same breast placement.

Description of the Prior Art

X-ray devices for performing tomosynthesis scans for producing 3-D slice images of the human breast are known. These devices are used predominantly in the field of diagnostics. By contrast, for screening, however, it is still predominantly 2-D mammography recordings that are generated by appropriately designed mammography x-ray devices. It is also known to calculate a synthetic mammogram from a tomosynthesis scan, but this is not considered to be a full-fledged equivalent to a conventional mammogram.

X-ray devices, with which it is possible to produce both 3-D tomosynthesis recordings and 2-D mammography recordings, are also known, particularly for enabling a simple comparison with previous recordings. An advantage of these combined tomosynthesis devices is that it is possible to produce both the mammogram and the tomosynthesis scan with the same position of the breast, i.e., with an identical compression of the breast.

It is well known that, during digital mammography, the radiation emanating from the x-ray radiation source is incident on the breast as the object to be irradiated and is subsequently incident on the x-ray radiation detector. Here, a distinction is made between the primary radiation, which supplies the information that is decisive for the x-ray image, and the scattered radiation. The scattered radiation causes more image noise and reduces the quality of the image contrast and hence also the image quality. In order to remedy this, mammography devices are equipped with anti-scatter grids. These are attached between the breast and the x-ray radiation detector and absorb the scattered radiation, but simultaneously also absorb some of the decisive primary radiation. Consequently, the organ dose must be adapted accordingly in order to obtain the desired image quality. For the patient, this means an additional radiation exposure.

The problem of the dose being increased by the use of an anti-scatter-grid also exists in the multimode x-ray devices known in the prior art because, in that case, an anti-scatter grid is also situated in the beam path in order to absorb the scattered radiation when producing the mammogram. In order nevertheless to achieve the desired image quality, a higher radiation exposure has therefore always been required in multimode x-ray devices.

SUMMARY OF THE INVENTION

An object of the present invention is to keep the radiation exposure as low as possible in multimode x-ray devices.

The advantages and embodiments explained below in the context of the method apply analogously to the x-ray system according to the invention, and vice versa.

According to the invention, in the method, all recordings are produced without the use of an anti-scatter grid, and a retroactive scattered radiation correction is implemented. Consequently, an anti-scatter grid is used neither in the 2-D recording mode nor in the 3-D recording mode of the multimode x-ray device. The multimode x-ray device is distinguished by an anti-scatter-grid-free beam path between the x-ray radiation source and the x-ray radiation detector during the production of all recordings, and by a processor that performs a retroactive scattered radiation correction. Expressed differently, an anti-scatter grid is never situated between the x-ray radiation source and the x-ray radiation detector. Since all recordings are produced without the use of an anti-scatter grid, the x-ray device does not have such an anti-scatter grid from the outset.

The invention therefore makes available a method and x-ray device for generating a grid-free mammography recording within a tomosynthesis scan with the same breast position, i.e. with identical compression of the breast. The most important advantage of this technique is significantly reducing the dose, typically by up to 30 percent, as a result of dispensing with the anti-scatter grid and the higher radiation exposure associated therewith. Using the invention, the radiation exposure can also be kept as low as possible in multimode x-ray devices. In contrast to synthetically generated mammograms, a full-fledged, "real" (non-synthetic) mammogram is produced in the present invention by the 2-D recording within a tomosynthesis recording procedure at the lowest possible dose.

A further advantage of the invention is that the manufacturing cost of the multimode x-ray device is reduced because the anti-scatter grid, as an additional component of the x-ray device, is dispensed with. At the same time, this dispenses with a possible source of error, as a result of which the reliability of the x-ray device is increased. This applies, in particular, to the drive and transmission units, which are responsible in conventional devices for the grid movement of the anti-scatter grid in the operational position thereof.

Since it is no longer necessary in the invention to move the anti-scatter grid in the operational position thereof, this also dispenses with the potential causes for interference with the image quality by artefacts, for example as a result of electrostatic interactions or the like.

Dispensing with the anti-scatter grid is also advantageous because the times for the backward and forward movement of the anti-scatter grid from a parked position to the operational position thereof between the breast and the x-ray radiation detector do not occur. This leads to a shortening of the recording procedure. The breast is compressed for a shorter period of time, and so the entire method is less uncomfortable for the patient.

The present invention not only serves to reduce the radiation exposure by a mammography recording performed without a grid within the scope of a tomosynthesis scan, but also provides various ways for optimizing a subsequently used scattered radiation correction.

In a first embodiment of the invention, there is a retroactive scattered radiation correction, i.e., it is executed following the production of the recordings, with the execution of an image processing algorithm in a suitable correction unit supplied with the data necessary for this purpose. The algorithm corrects the scattered radiation retroactively by identifying the regions generated by scattered radiation and removing these from the image by calculation. By contrast, the decisive primary radiation is entirely maintained. Consequently, the anti-scatter grid becomes superfluous and a lower dose is sufficient for obtaining high-quality images.

Depending on the thickness of the compressed breast, the radiation dose can typically be reduced by up to 30 percent using such a grid-free recording technique. Such a software solution is commercially available from Siemens Healthcare under the trade name Siemens Inspiration PRIME (Progressive Reconstruction, Intelligently Minimizing Exposure).

This type of software is not required in a second embodiment of the invention. Rather, a scattered radiation correction is subsequently implemented by means of a suitable correction unit, exclusively by using a synthetic 2-D recording which was previously generated from the produced 3-D recordings of the multimode x-ray device. Expressed differently, the tomosynthesis data are used for the scattered radiation correction. Since the slices are reconstructed by filtered back projection, i.e. the volume slices of the 3-D tomosynthesis scan resulting in a slice stack, are substantially free from scattered radiation due to the suppression of the low-frequency image components, they can be used for estimating the scattered radiation image. By way of example, it is possible to calculate the difference between, firstly, a synthetic mammogram calculated from the slices and, secondly, the measured center projection (projection angle 0°). This scattered radiation image is then subtracted from the mammogram recorded without a grid.

In a third embodiment of the invention, the generated synthetic 2-D recording can also be used in conjunction with that software-based scattered radiation correction which is implemented with the aid of an image processing algorithm, e.g. Siemens PRIME. For example, this can proceed in an appropriately adapted, suitable correction unit in such a way that the synthetic 2-D recording is used to check the image processing and optionally to optimize the latter. Or else there is a further scattered radiation correction using the synthetic 2-D recording following the scattered radiation correction implemented with the use of the image processing algorithm.

BRIEF DESCRIPTION OF THE DRAWINGS

FIG. 5 shows the sequence of a second scattered radiation correction.

FIG. 6 shows the sequence of a third scattered radiation correction.

DESCRIPTION OF THE PREFERRED EMBODIMENTS

All figures show the invention merely schematically and with the basic components thereof. The same reference signs correspond to elements with the same or a comparable function.

Figure 1:
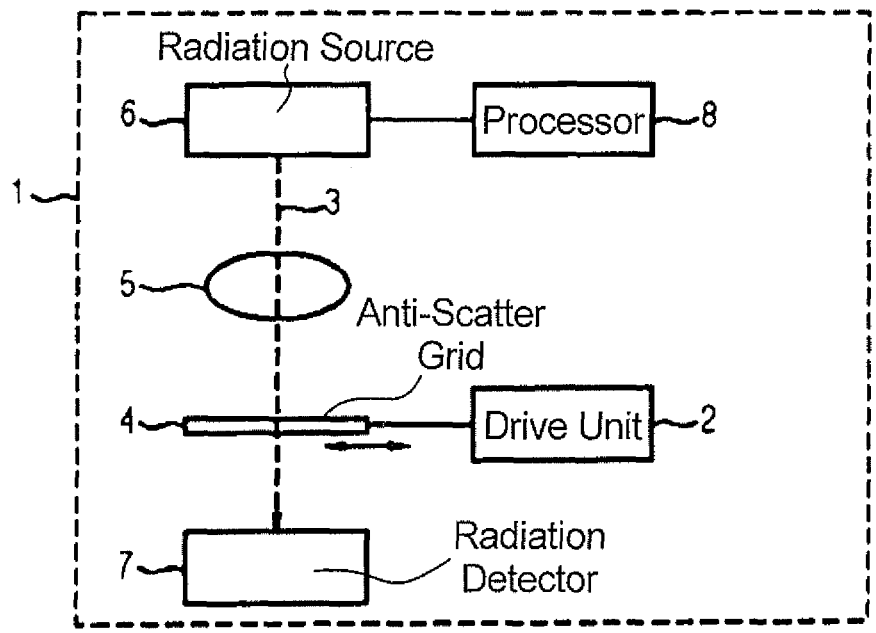
FIG. 1 shows a multimode x-ray device known from the prior art.
Figure 2:
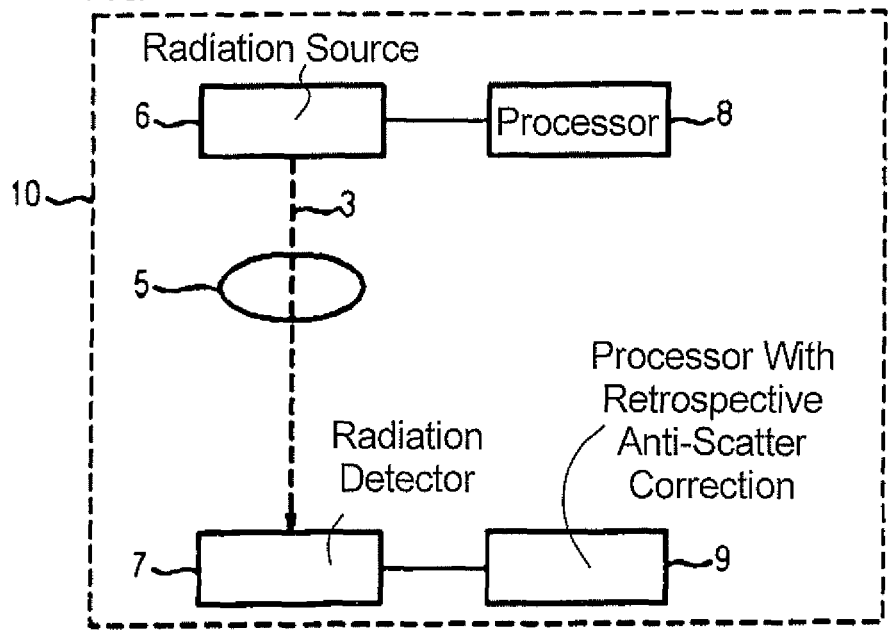
FIG. 2 shows a multimode x-ray device according to the invention.

FIG. 1 shows a multimode x-ray device 1, as is known from the prior art, that has an anti-scatter grid 4, that is insertable into the beam path 3 with the use of a drive unit 2, when required. The anti-scatter grid 4 and drive unit 2 are dispensed within the multimode x-ray device 10 according to the invention, as is depicted in FIG. 2. The multimode x-ray device 10 is operable in two recording modes. It is embodied to produce 2-D recordings and 3-D recordings of a breast 5 of a patient. It has an x-ray radiation source 6 and an x-ray radiation detector 7. The breast 5 is placed between the x-ray radiation source 6 and the x-ray radiation detector 7. The 2-D recordings and the 3-D recordings are producible with the same breast placement.

Figure 3:
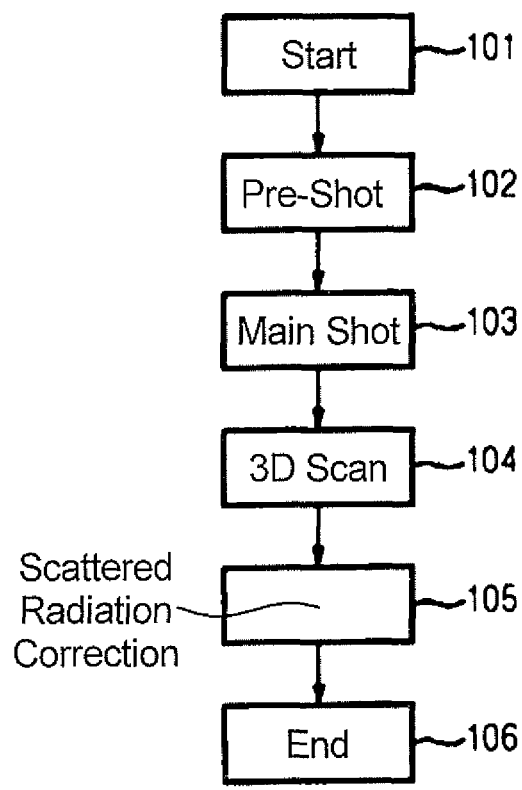
FIG. 3 shows the sequence of a method according to the invention.

As depicted in FIG. 3, there initially is a grid-free pre-recording after the start of the method (step 101), wherein the parameters, in particular the correct exposure time etc., required for producing an overall image with an ideal image quality are determined in a suitable processor 8 from this pre-shot. The pre-shot is typically recorded in the central projection (0°), in which the x-ray tube serving as x-ray radiation source 6 is arranged orthogonal to the breast 5. There is an AEC (automatic exposure control) calculation for the tomography scan and the main shot after this grid-free pre-shot. These preparing measures are combined in step 102 in FIG. 3.

Subsequently, the 2-D main recording, from which the mammogram is then generated, is produced in a grid-free manner, likewise in the 0° position, taking into account this automatic exposure (step 103). The otherwise conventional retraction of the anti-scatter grid 4 after the main shot and prior to introducing the tomography scan is dispensed with.

The 3-D tomosynthesis recording is subsequently implemented, likewise in an entirely grid-free manner, with the same position of the breast 5 and without an intermediate decompression of the breast 5 (step 104). Here, e.g. 25 recordings are generated from a −25° position to a +25° position, i.e. 25 individual shots with the spacing of 2°. From this, a stack of tomosynthesis slices and therefore 3-D volume is calculated. Therefore, the beam path 3 between the x-ray radiation source 6 and the x-ray radiation detector 7 remains anti-scatter-grid-free both during the production of the 2-D recording and during the production of the 3-D recordings.

Performing the recordings is followed by measures for scattered radiation correction, which are performed in a suitable processor 9 (step 105). After the scattered radiation correction, the method finishes (step 106).

Figure 4:
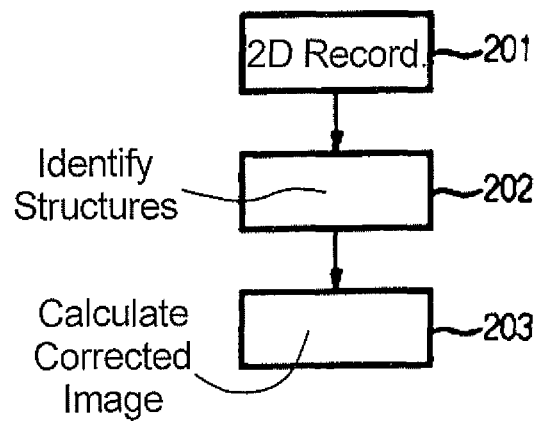
FIG. 4 shows the sequence of a first scattered radiation correction.

Here, the scattered radiation correction within step 105 is implemented in the functional unit 9, for example, as depicted in FIG. 4, by a suitable image processing algorithm such as e.g. Siemens PRIME. In such a software solution, the produced 2-D recording is read (step 201). Subsequently, an algorithm identifies the structures responsible for the scattered radiation (step 202) and calculates a corrected image (step 203). While the scattered radiation is removed by calculation, the primary radiation can be used in its entirety.

Alternatively, the scattered radiation correction within step 105 is implemented, as depicted in FIG. 5, by virtue of an always scattered radiation-free synthetic mammogram being initially calculated (step 302) in the functional unit 9 from the 3-D volume of the tomosynthesis scan, i.e. by using the tomosynthesis data, after the provision of the 3-D recordings (step 301). In step 302, a mammogram is generated by means of a back projection from volume data obtained by tomosynthesis. Expressed differently, all slices of the 3-D scan are integrated to form a synthetic 2-D image. Subsequently, in the computer 9, the calculated synthetic mammogram is subtracted from the mammogram recorded in a grid-free manner, as a result of which the scattered radiation portion is established (step 303). Subsequently, the mammogram recorded in a grid-free manner is reduced by this established scattered radiation portion in order to obtain a corrected mammogram (step 304).

In a further variant, as depicted in FIG. 6, there is, in addition to the already aforementioned scattered radiation correction by the software algorithm (steps 201 to 203), a calculation of the residual scattered radiation portion of the mammogram, which was already corrected by the software with the aid of the synthetic mammogram generated in steps 301 and 302, in the processor 9 and within step 105 (step 401). Subsequently, a check is carried out as to whether the scattered radiation portion established computationally by the algorithm corresponds to the actual scattered radiation portion established by the synthetic mammogram (step 402). There optionally is an optimization of the software-based scattered radiation correction (step 403) such that the image quality is improved. Subsequently, there is correspondingly optimized image post-processing (step 404). By way of example, there is noise suppression and/or image post-processing parameters are adapted accordingly.

The multimode x-ray device 10 according to the invention is embodied for performing the above-described method. Preferably, the processor 8 and the processor 9 for the scattered radiation correction are data processing units, which are embodied to perform all steps corresponding to the method, described herein, which are connected to the processing of data. The data processing units preferably have a number of functional modules, wherein each functional module is embodied for performing a specific function or a number of specific functions in accordance with the above-described method. By way of example, the processor 9 has a calculation module for calculating the synthetic mammogram in step 302. The processors 8, 9 can be hardware modules or software modules. Expressed differently, the invention, to the extent that it relates to the data processing unit, can be implemented in the form of computer hardware or in the form of computer software or in a combination of hardware and software. To the extent that the invention is implemented in the form of software, i.e. as a computer program, all above-described functions are implemented by computer program instructions when the computer program is executed on a computer with a processor. This relates, in particular, to computer program instructions for generating the synthetic 2-D recording from the produced 3-D recordings in step 302, computer program instructions for the retrospective scattered radiation correction using the synthetic 2-D recording in step 105, computer program instructions for the retrospective scattered radiation correction with the aid of an image processing algorithm in steps 202 and 203, and computer program instructions for the scattered radiation correction using the synthetic 2-D recording in steps 303 and 304 or for performing a further scattered radiation correction, following a first scattered radiation correction, using the synthetic 2-D recording in steps 401 to 404. Here, the computer program instructions are implemented in a manner known per se in any programming language and can be provided to the computer in any form, for example in the form of data packets, which are transmitted via a computer network, or in the form of a computer program stored on a disk, a CD-ROM or any other data medium.

Although modifications and changes may be suggested by those skilled in the art, it is the intention of the inventor to embody within the patent warranted hereon all changes and modifications as reasonably and properly come within the scope of his contribution to the art.

We claim as our invention:

1. A mammography method comprising:

operating an x-ray source to irradiate a breast with x-rays that produce scattered radiation, and detecting x-rays attenuated by the breast, with no anti-scatter grid between the x-ray source and the radiation detector, so as to produce a 2D mammogram of the breast, said 2D mammogram comprising a scattered radiation contribution;

operating said x-ray source to again irradiate the breast with x-rays that produce scattered radiation, and detecting x-rays attenuated by the breast, with no anti-scatter grid between the x-ray source and the radiation detector, while the ray source is moved through a plurality of projection directions relative to the breast, and thereby obtaining a plurality of projection images that each have a scattered radiation contribution, with a position of the breast while acquiring said projection images being unchanged from a position of the breast while acquiring said 2D mammogram;

providing said two mammogram and said plurality of projection images to a processor and, in said processor, generating a 3D image of the breast from said projection images, which includes the respective scattered radiation contributions in the projection images;

in said processor, applying a retrospective scattered radiation correction algorithm to said 3D image in order to remove said scattered radiation contribution from said 3D image, thereby obtaining a scatter-corrected 3D image;

in said processor, generating a synthetic 2D mammogram from said projection images by executing a tomosynthesis algorithm that causes the scattered radiation contributions in the respective projection images not to be present in the synthetic 2D mammogram;

in said processor, forming a difference image between said 2D mammogram and said synthetic 2D mammogram in order to obtain a corrected 2D mammogram from which said scattered radiation contributions have been removed; and making the corrected 3D image and the corrected 2D mammogram available from the computer in electronic form as respective data files.

2. A mammography method as claimed in claim 1 comprising generating said synthetic 2D mammogram using a filtered backprojection reconstruction algorithm as said tomosynthesis algorithm.

3. An x-ray mammography apparatus comprising:

an imaging system consisting of an x-ray source and a radiation detector situated on opposite sides of breast;

a computer configured to operate the imaging system in order to irradiate a breast with x-rays from the x-ray source that produce scattered radiation, and to detect x-rays attenuated by the breast with the radiation detector, with no anti-scatter grid between the x-ray source and the radiation detector, so as to produce a 2D mammogram of the breast, said 2D mammogram comprising a scattered radiation contribution;

said computer being configured to operate the imaging system in order to again irradiate the breast with x-rays from the x-ray source that produce scattered radiation, and to detect x-rays attenuated by the breast with said radiation detector, with no anti-scatter grid between the x-ray source and the radiation detector, while the x-ray source is moved through a plurality of projection directions relative to the breast, and thereby obtain a plurality of projection images that each have a scattered radiation contribution, with a position of the breast while acquiring said projection images being unchanged from a position of the breast while acquiring said 2D mammogram;

said computer being configured to generate a 3D image of the breast from said plurality of projection images, which includes the respective scattered radiation contributions in the projection images;

said computer being configured to apply a retrospective scattered radiation correction algorithm to said 3D image in order to remove said scattered radiation contribution from said 3D image, thereby obtaining a scatter-corrected 3D image;

said computer being configured to generate a synthetic 2D mammogram from said projection images by executing a tomosynthesis algorithm that causes the scattered radiation contributions in the respective projection images not to be present in the synthetic 2D mammogram;

said computer being configured to form a difference image between said 2D mammogram and said synthetic 2D mammogram in order to obtain a scatter-corrected 2D mammogram from which said scattered radiation contributions have been removed; and making the scatter-corrected 3D image and the scatter-corrected 2D mammogram available from the computer in electronic form as respective data files.

4. An x-ray mammography apparatus as claimed in claim 3 wherein said computer is configured to generate said synthetic 2D mammogram using a filtered backprojection reconstruction algorithm as said tomosynthesis algorithm.

* * * * *